US011325560B2

(12) United States Patent
Sawai et al.

(10) Patent No.: US 11,325,560 B2
(45) Date of Patent: May 10, 2022

(54) ATTENTION CALLING DEVICE AND ATTENTION CALLING SYSTEM

(71) Applicants: TOYOTA JIDOSHA KABUSHIKI KAISHA, Toyota (JP); KABUSHIKI KAISHA TOKAI RIKA DENKI SEISAKUSHO, Aichi (JP)

(72) Inventors: Shunichiroh Sawai, Numazu (JP); Toshihiro Tsutsui, Aichi-ken (JP)

(73) Assignees: TOYOTA JIDOSHA KABUSHIKI KAISHA, Toyota (JP); KABUSHIKI KAISHA TOKAI RIKA DENKI SEISAKUSHO, Aichi (JP)

( * ) Notice: Subject to any disclaimer, the term of this patent is extended or adjusted under 35 U.S.C. 154(b) by 128 days.

(21) Appl. No.: 16/715,361

(22) Filed: Dec. 16, 2019

(65) Prior Publication Data
US 2020/0189518 A1  Jun. 18, 2020

(30) Foreign Application Priority Data
Dec. 18, 2018  (JP) .............................. JP2018-236340

(51) Int. Cl.
| B65H 75/00 | (2006.01) |
| B60R 22/34 | (2006.01) |
| A61B 5/18 | (2006.01) |
| B60Q 9/00 | (2006.01) |

(52) U.S. Cl.
CPC ................. *B60R 22/34* (2013.01); *A61B 5/18* (2013.01); *B60Q 9/00* (2013.01)

(58) Field of Classification Search
CPC ......... A61B 5/0077; A61B 5/18; A61B 5/746; B60Q 9/00; B60R 22/34; G08B 21/06
USPC .......................................................... 242/370
See application file for complete search history.

(56) References Cited

U.S. PATENT DOCUMENTS

| 10,207,640 | B2 * | 2/2019 | Bachorski | ............. B60W 50/16 |
| 2007/0029772 | A1 * | 2/2007 | Takao | ..................... B60R 22/46 |
| | | | | 280/801.1 |
| 2016/0246298 | A1 * | 8/2016 | Sato | ........................ B60Q 5/005 |
| 2017/0313319 | A1 * | 11/2017 | Kishi | ..................... B60W 30/08 |
| 2018/0141570 | A1 * | 5/2018 | Kimura | ................. B60W 50/16 |
| 2019/0232966 | A1 * | 8/2019 | Prakah-Asante | ..... B60W 50/14 |
| 2019/0276047 | A1 * | 9/2019 | Suzuki | ................... B60W 50/14 |

(Continued)

FOREIGN PATENT DOCUMENTS

JP    2017-228280 A    12/2017

*Primary Examiner* — Naomi J Small
(74) *Attorney, Agent, or Firm* — Sughrue Mion, PLLC

(57) ABSTRACT

An attention calling device is configured to call attention of a driver of a vehicle with a drive mode switchable among manual driving, drive assist, and driver-centered automated driving. The attention calling device includes: a drive mode recognition unit configured to recognize the drive mode being executed; a driver state recognition unit configured to recognize a driver state based on a captured image from a driver monitor camera provided in the vehicle; a determination unit configured to determine based on the driver state whether it is necessary to call the attention; and a control unit configured to control a stimulus application device of the vehicle so as to apply a stimulus at an intensity that matches the drive mode being executed to the driver to direct the attention of the driver to driving of the vehicle when the determination unit determines that it is necessary to call the attention.

10 Claims, 2 Drawing Sheets

(56) References Cited

U.S. PATENT DOCUMENTS

2019/0283756 A1\* 9/2019 Leonard ............ B60W 30/0956
2020/0025575 A1\* 1/2020 Weissman ............. G01S 13/751
2020/0134379 A1\* 4/2020 Gaidon ................ G08G 1/0112

\* cited by examiner

ATTENTION CALLING DEVICE AND ATTENTION CALLING SYSTEM

INCORPORATION BY REFERENCE

The disclosure of Japanese Patent Application No. 2018-236340 filed on Dec. 18, 2018 including the specification, drawings and abstract is incorporated herein by reference in its entirety.

BACKGROUND

1. Technical Field

The disclosure relates to an attention calling device and an attention calling system.

2. Description of Related Art

There is proposed an attentiveness maintenance device that temporally fluctuates the intensity of a stimulus for maintaining a target person in an attentive state in the case where a trigger detection unit detects a predetermined trigger (Japanese Patent Application Publication No. 2017-228280 (JP 2017-228280 A), for example).

SUMMARY

If a stimulus at a constant intensity is applied to a driver to direct his/her attention to driving, for example, in a vehicle with its drive mode switchable among manual driving, drive assist, and driver-centered automated driving, the intensity of the stimulus may not be suitable for the driver, and the driver may be annoyed with the stimulus.

The disclosure provides an attention calling device and an attention calling system that can suppress a driver feeling annoyed with a stimulus applied to the driver in order to call the attention of the driver.

A first aspect of the disclosure provides an attention calling device. The attention calling device is configured to call attention of a driver of a vehicle with a drive mode switchable among manual driving, drive assist, and driver-centered automated driving. The attention calling device includes: a drive mode recognition unit configured to recognize the drive mode being executed; a driver state recognition unit configured to recognize a driver state, which is a state of the driver, based on a captured image from a driver monitor camera provided in the vehicle; a determination unit configured to determine based on the driver state whether it is necessary to call the attention; and a control unit configured to control a stimulus application device of the vehicle so as to apply a stimulus at an intensity that matches the drive mode being executed to the driver to direct an attention of the driver to driving of the vehicle in the case where the determination unit determines that it is necessary to call the attention.

A second aspect of the disclosure provides an attention calling device. The attention calling device includes at least one processor. The processor is configured to: recognize a drive mode being executed in a vehicle; recognize a driver state which is a state of a driver of the vehicle; determine based on the driver state whether it is necessary to call attention; and output a signal for applying a stimulus at an intensity that matches the drive mode being executed to the driver to direct an attention of the driver to driving of the vehicle in the case where it is determined that it is necessary to call the attention.

In the aspect described above, the processor may be configured to output the signal so as to make the intensity of the stimulus which is applied to the driver higher as the drive mode being executed is a drive mode that provides less opportunities for the driver to be involved in drive operations for the vehicle.

In the aspect described above, the drive mode may include manual driving, drive assist, and driver-centered automated driving. The processor may be configured to: output the signal such that the intensity of the stimulus which is applied to the driver in the case where the drive mode is the manual driving is less than that of the stimulus which is applied in the case where the drive mode is the drive assist; and output the signal such that the intensity of the stimulus which is applied to the driver in the case where the drive mode is the drive assist is less than that of the stimulus which is applied in the case where the drive mode is the driver-centered automated driving.

In the aspect described above, the drive mode may include system-centered automated driving. The processor may be configured to output the signal such that the intensity of the stimulus which is applied to the driver in the case where the drive mode is the system-centered automated driving is less than that of the stimulus which is applied in the case where the drive mode is the driver-centered automated driving.

A third aspect of the disclosure provides an attention calling system. The attention calling system includes: a camera configured to acquire a captured image of a driver of a vehicle; a stimulus application device configured to apply a stimulus to the driver; and at least one processor. The processor may be configured to: recognize a drive mode being executed in the vehicle; recognize a driver state, which is a state of the driver, based on the image which is acquired by the camera; determine based on the driver state whether it is necessary to call attention; and control the stimulus application device so as to apply a stimulus at an intensity that matches the drive mode being executed to the driver to direct an attention of the driver to driving of the vehicle in the case where it is determined that it is necessary to call the attention.

In the aspect described above, the processor may be configured to make the intensity of the stimulus which is applied to the driver higher as the drive mode being executed is a drive mode that provides less opportunities for the driver to be involved in drive operations for the vehicle.

In the aspect described above, the drive mode may include manual driving, drive assist, and driver-centered automated driving. The processor may be configured to: control the stimulus application device such that the intensity of the stimulus which is applied to the driver in the case where the drive mode is the manual driving is less than that of the stimulus which is applied in the case where the drive mode is the drive assist; and control the stimulus application device such that the intensity of the stimulus which is applied to the driver in the case where the drive mode is the drive assist is less than that of the stimulus which is applied in the case where the drive mode is the driver-centered automated driving.

In the aspect described above, the drive mode may include system-centered automated driving. The processor may be configured to control the stimulus application device such that the intensity of the stimulus which is applied to the driver in the case where the drive mode is the system-centered automated driving is less than that of the stimulus which is applied in the case where the drive mode is the driver-centered automated driving.

In the aspect described above, the stimulus application device may be a retractor configured to wind a seatbelt. The retractor may be configured to wind the seatbelt more strongly as the intensity of the stimulus which is applied to the driver is higher.

With the disclosure, it is possible to suppress a driver feeling annoyed with a stimulus applied to the driver in order to call the attention of the driver.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

An exemplary embodiment will be described below with reference to the drawings.

Figure 1:
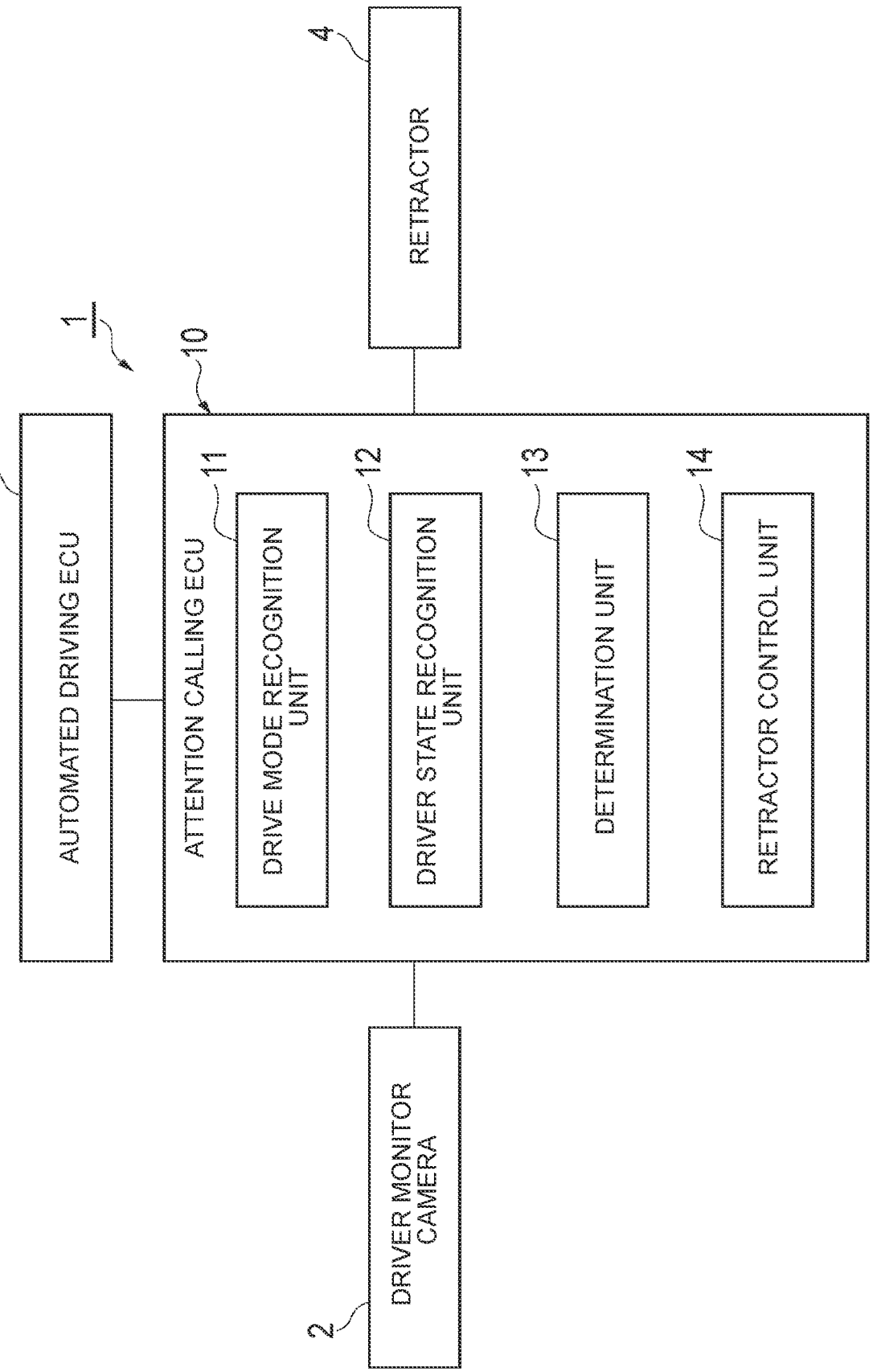
FIG. 1 is a block diagram illustrating an attention calling device according to an embodiment.

FIG. 1 is a block diagram illustrating an attention calling device 1 according to an embodiment. By way of example, the attention calling device 1 illustrated in FIG. 1 is a device mounted on a vehicle such as a passenger car that can be driven through automated driving to provide a driver with a stimulus for calling the attention of the driver. The automated driving is vehicle control for causing the vehicle to automatically travel to a destination set in advance.

The attention calling device 1 includes an attention calling electronic control unit (ECU) 10 that integrally controls the device. The attention calling ECU 10 is an electronic control unit that has a central processing unit (CPU), a read only memory (ROM), a random access memory (RAM), etc. The attention calling ECU 10 implements various functions related to an attention calling process by the RAM loading a program stored in the ROM and the CPU executing the program which has been loaded into the RAM, for example. The attention calling ECU 10 may be constituted from a plurality of ECUs. Some of the functions of the attention calling ECU 10 may be executed by a server that can communicate with the vehicle.

A driver monitor camera 2, an automated driving ECU 3, and a retractor (stimulus application device) 4 are connected to the attention calling ECU 10.

The driver monitor camera 2 is a device that captures an image of the driver. The driver monitor camera 2 is provided in front of the driver and above a cover of a steering column of the vehicle to capture an image of at least the face of the driver. In order to capture images of the driver from a plurality of directions, a plurality of driver monitor cameras 2 may be provided at locations other than the steering column. The driver monitor camera 2 transmits captured image information on the driver to the attention calling ECU 10.

The automated driving ECU 3 is an electronic control unit that executes automated driving of the vehicle. The automated driving ECU 3 is an electronic control unit that has a CPU, a ROM, a RAM, etc. The automated driving ECU 3 implements various functions of automated driving by the RAM loading a program stored in the ROM and the CPU executing the program which has been loaded into the RAM, for example. The automated driving ECU 3 may be constituted from a plurality of ECUs. Some of the functions of the automated driving ECU 3 may be executed by a server that can communicate with the vehicle.

The automated driving ECU 3 generates a travel plan along a target route to a destination set in advance based on position information on the vehicle measured by a Global Positioning System (GPS) reception unit mounted on the vehicle, map information from a map database, the surrounding environment of the vehicle (such as positions of other vehicles) which is recognized from the results of detection by an external camera and a radar sensor (millimeter-wave radar and lidar) mounted on the vehicle, and the vehicle state (such as a vehicle speed and a yaw rate) which is recognized from the results of detection by internal sensors (such as a vehicle speed sensor and a yaw rate sensor) mounted on the vehicle. The destination may be set by an occupant etc. The target route may be set by a known navigation system based on the destination. In this case, the navigation system may be integral with the automated driving ECU 3.

The automated driving ECU 3 executes automated driving toward the destination in accordance with the travel plan. The automated driving ECU 3 executes automated driving by transmitting a control signal to actuators (such as an engine actuator, a steering actuator, and a brake actuator) of the vehicle.

The automated driving ECU 3 is configured to be able to switch among a plurality of drive modes. The drive modes are classified in advance in accordance with the degree of involvement of the driver in drive of the vehicle, and include manual driving, drive assist, driver-centered automated driving, and system-centered automated driving. The automated driving ECU 3 transmits drive mode information to the attention calling ECU 10.

By way of example, the manual driving is a drive mode in which the driver is required to hold a steering wheel and the driver is required to perform all the steering operation, accelerator pedal operation, and brake pedal operation.

The drive assist is a drive mode in which the driver is required to hold the steering wheel and at least one of the steering operation, accelerator pedal operation, and brake pedal operation is automatically controlled so that the driver is not required to perform such an operation. Examples of the drive assist include adaptive cruise control (ACC) and lane keeping assist (LKA).

The driver-centered automated driving is a drive mode in which the driver is not required to hold the steering wheel, all the steering operation, accelerator pedal operation, and brake pedal operation are automatically controlled so that the driver is not required to perform such operations, and the driver takes the initiative to drive the vehicle. In the driver-centered automated driving, the driver is not required to perform vehicle drive operations themselves, but is required to monitor the surrounding situation, the vehicle behavior, etc. during the automated driving of the vehicle, and intervene in the automated driving as necessary.

The system-centered automated driving is a drive mode in which the driver is not required to hold the steering wheel, all the steering operation, accelerator pedal operation, and brake pedal operation are automatically controlled so that the driver is not required to perform such operations, and the automated driving ECU 3 (automated driving system) takes the initiative to drive the vehicle. In the system-centered automated driving, the driver is not required to perform vehicle drive operations themselves, and is not necessarily required to monitor the surrounding situation, the vehicle behavior, etc. during the automated driving of the vehicle.

The retractor 4 is an actuator that winds and unwinds a seatbelt of the vehicle. The retractor 4 is provided for at least a seatbelt of a driver's seat of the vehicle. The retractor 4 winds the seatbelt in accordance with a control signal from the attention calling ECU 10. The retractor 4 varies the tension of the seatbelt by winding the seatbelt in accordance with an intensity that matches the control signal from the attention calling ECU 10. Consequently, a stimulus applied to the driver can be varied.

Next, the functional configuration of the attention calling ECU 10 will be described. The attention calling ECU 10 has a drive mode recognition unit 11, a driver state recognition unit 12, a determination unit 13, and a retractor control unit (control unit) 14.

The drive mode recognition unit 11 recognizes the drive mode being executed based on the drive mode information from the automated driving ECU 3.

The driver state recognition unit 12 recognizes the driver state based on the captured image from the driver monitor camera 2. The driver state means the state of the driver which is utilized to determine whether it is necessary to call the attention of the driver.

The driver state recognition unit 12 acquires the direction of the face of the driver using a known image processing method based on the captured image information from the driver monitor camera 2, for example, and acquires angle information on the direction of the face of the driver for each of the yaw angle direction, the pitch angle direction, and the roll direction. The driver state recognition unit 12 recognizes whether the driver is looking away using a known method based on the angle information on the direction of the face of the driver. Looking away means a state in which the driver is looking away from a predetermined range such as the front, for example. The driver state recognition unit 12 recognizes the driver looking away, as the driver state, in the case where the direction of the face of the driver deviates from the direction of the front of the driver by an angle set in advance or more in the yaw angle direction, the pitch angle direction, or the roll direction over a time set in advance, for example.

The driver state recognition unit 12 recognizes the degree of attentiveness of the driver in accordance with the rate of closure of the eyes of the driver per minute, the status of opening of the eyes, the frequency of blinking, eye motion, the degree of temporal variations in the direction of the face, the presence or absence of yawning action, the degree of variations in the degree of opening of the mouth, etc. using a known image processing method based on the captured image information from the driver monitor camera 2, for example. The degree of attentiveness is a degree that indicates how the driver is attentive, rather than being faint because of a lack of sleep etc. The driver state recognition unit 12 recognizes a reduced degree of attentiveness of the driver, as the driver state, in the case where the degree of attentiveness is a predetermined threshold or less, for example.

The driver state recognition unit 12 acquires the direction of the line of sight of the driver using a known image processing method based on the captured image information from the driver monitor camera 2, for example, and recognizes whether the driver is driving carelessly. Driving carelessly indicates a state in which the driver is thinking about something, for example, and means a state in which the driver does not feel significantly drowsy but fails to check the surroundings of the driver. The driver state recognition unit 12 recognizes the driver driving carelessly, as the driver state, when the variations in the direction of the line of sight of the driver or the direction of the face remain in a predetermined range over a time set in advance in the case where the degree of attentiveness is not equal to or less than a predetermined threshold, for example.

The determination unit 13 determines, based on the driver state which is recognized by the driver state recognition unit 12, whether it is necessary to call attention. The determination unit 13 determines that it is necessary to call attention in the case where the driver state recognition unit 12 recognizes the driver looking away, for example. The determination unit 13 determines that it is necessary to call attention in the case where the driver state recognition unit 12 recognizes a reduced degree of attentiveness of the driver, for example. The determination unit 13 determines that it is necessary to call attention in the case where the driver state recognition unit 12 recognizes the driver driving carelessly, for example.

The retractor control unit 14 controls the retractor 4 so as to apply a stimulus at an intensity that matches the drive mode being executed, which is recognized by the drive mode recognition unit 11, to the driver to direct the attention of the driver to driving of the vehicle in the case where the determination unit 13 determines that it is necessary to call attention. The retractor control unit 14 determines which of the manual driving, the drive assist, the driver-centered automated driving, and the system-centered automated driving the drive mode being executed is based on the drive mode which is recognized by the drive mode recognition unit 11.

The retractor control unit 14 controls the retractor 4 so as to apply a stimulus at an intensity ST1, as the intensity that matches the drive mode being executed, to the driver in the case where it is determined that the drive mode being executed is the manual driving. The retractor control unit 14 controls the retractor 4 so as to apply a stimulus at an intensity ST2, as the intensity that matches the drive mode being executed, to the driver in the case where it is determined that the drive mode being executed is the drive assist. The retractor control unit 14 controls the retractor 4 so as to apply a stimulus at an intensity ST3, as the intensity that matches the drive mode being executed, to the driver in the case where it is determined that the drive mode being executed is the driver-centered automated driving. The retractor control unit 14 controls the retractor 4 so as to apply a stimulus at an intensity ST4, as the intensity that matches the drive mode being executed, to the driver in the case where it is determined that the drive mode being executed is the system-centered automated driving. The intensities ST1 to ST4 are intensities at which the retractor control unit 14 causes the retractor 4 to wind the seatbelt for the driver's seat in accordance with the drive mode being executed.

By way of example, the intensity ST2 is higher than the intensity ST1. The intensity ST3 is higher than the intensity ST2. That is, the intensity of a stimulus applied to the driver becomes higher in the order of a case where the drive mode is the manual driving, a case where the drive mode is the drive assist, and a case where the drive mode is the driver-centered automated driving. The reason for this order is that it is considered that the driver tends to feel drowsy in accordance with the degree to which the attention of the driver is directed to driving in each drive mode. For example, it is considered that the relative time before the drowsiness of the driver at the same degree of attentiveness reaches a predetermined level or higher becomes shorter in the order discussed above. That is, it is considered that the driver tends to feel drowsy or drive carelessly more often in a drive mode that provides less opportunities for the driver to be involved in drive operations for the vehicle.

Meanwhile, the intensity ST4 is lower than the intensity ST3, for example. That is, the intensity of a stimulus applied to the driver is lower in the case where the drive mode is the system-centered automated driving than in the case where the drive mode is the driver-centered automated driving. The reason for this order is that it is considered that the driver tends to feel more drowsy in the case where the drive mode is the system-centered automated driving since the degree to which the attention of the driver is directed to driving in such a case is lower than in the case where the drive mode is the driver-centered automated driving. In consideration of the fact that the driver is not necessarily required to monitor the surrounding situation, the vehicle behavior, etc. during automated driving of the vehicle in the system-centered automated driving, however, it is considered that the intensity of a stimulus that should be applied to the driver in the system-centered automated driving can be lower than the intensity of a stimulus that should be applied to the driver in the driver-centered automated driving. The intensity ST4 may be lower than the intensity ST2. The intensity ST4 may be lower than the intensity ST1. The intensity ST4 may be an intensity at which no stimulus is applied to the driver.

Figure 2:
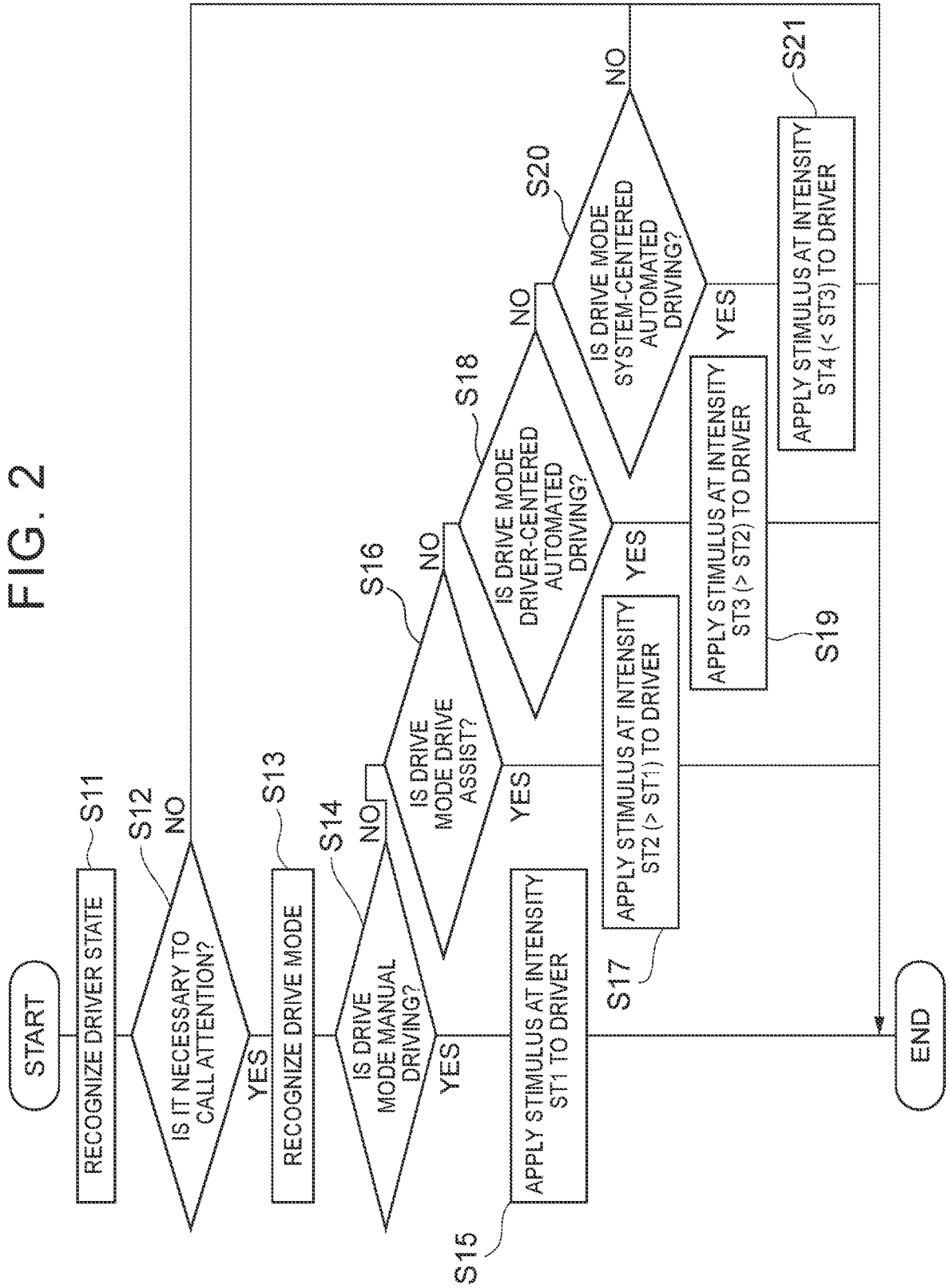
FIG. 2 is a flowchart illustrating an attention calling process.

Subsequently, the attention calling process by the attention calling ECU 10 will be described. FIG. 2 is a flowchart illustrating the attention calling process. The flowchart in FIG. 2 is executed during travel of the vehicle, for example.

As illustrated in FIG. 2, in step S11, the driver state recognition unit 12 of the attention calling ECU 10 recognizes the state of the driver using a known method based on the captured image information on the driver which is received from the driver monitor camera 2. In step S12, the determination unit 13 of the attention calling ECU 10 determines whether it is necessary to call attention based on the driver state which is recognized by the driver state recognition unit 12.

In the case where the determination unit 13 of the attention calling ECU 10 determines that it is necessary to call attention (S12: YES), the drive mode recognition unit 11 recognizes the drive mode being executed in step S13. In step S14, the retractor control unit 14 of the attention calling ECU 10 determines based on the drive mode which is recognized by the drive mode recognition unit 11 whether the drive mode is the manual driving.

In the case where the retractor control unit 14 of the attention calling ECU 10 determines that the drive mode is the manual driving (S14: YES), the retractor control unit 14 controls, in step S15, the retractor 4 so as to apply a stimulus at the intensity ST1 to the driver as the intensity that matches the manual driving which is the drive mode being executed. After that, the attention calling ECU 10 ends the current attention calling process, and executes the attention calling process again from step S11.

In the case where the retractor control unit 14 of the attention calling ECU 10 determines that the drive mode is not the manual driving (S14: NO), the retractor control unit 14 of the attention calling ECU 10 determines based on the drive mode which is recognized by the drive mode recognition unit 11 whether the drive mode is the drive assist in step S16.

In the case where the retractor control unit 14 of the attention calling ECU 10 determines that the drive mode is the drive assist (S16: YES), the retractor control unit 14 controls, in step S17, the retractor 4 so as to apply a stimulus at the intensity ST2, which is higher than the intensity ST1, to the driver as the intensity that matches the drive assist which is the drive mode being executed. After that, the attention calling ECU 10 ends the current attention calling process, and executes the attention calling process again from step S11.

In the case where the retractor control unit 14 of the attention calling ECU 10 determines that the drive mode is not the drive assist (S16: NO), the retractor control unit 14 of the attention calling ECU 10 determines based on the drive mode which is recognized by the drive mode recognition unit 11 whether the drive mode is the driver-centered automated driving in step S18.

In the case where the retractor control unit 14 of the attention calling ECU 10 determines that the drive mode is the driver-centered automated driving (S18: YES), the retractor control unit 14 controls, in step S19, the retractor 4 so as to apply a stimulus at the intensity ST3, which is higher than the intensity ST2, to the driver as the intensity that matches the driver-centered automated driving which is the drive mode being executed. After that, the attention calling ECU 10 ends the current attention calling process, and executes the attention calling process again from step S11.

In the case where the retractor control unit 14 of the attention calling ECU 10 determines that the drive mode is not the driver-centered automated driving (S18: NO), the retractor control unit 14 of the attention calling ECU 10 determines based on the drive mode which is recognized by the drive mode recognition unit 11 whether the drive mode is the system-centered automated driving in step S20.

In the case where the retractor control unit 14 of the attention calling ECU 10 determines that the drive mode is the system-centered automated driving (S20: YES), the retractor control unit 14 controls, in step S21, the retractor 4 so as to apply a stimulus at the intensity ST4, which is lower than the intensity ST3, to the driver as the intensity that matches the system-centered automated driving which is the drive mode being executed. After that, the attention calling ECU 10 ends the current attention calling process, and executes the attention calling process again from step S11.

In the case where the determination unit 13 of the attention calling ECU 10 determines that it is not necessary to call attention (S12: NO), on the other hand, the attention calling ECU 10 ends the current attention calling process, and executes the attention calling process again from step S11.

With the attention calling device 1, as has been described above, a stimulus at an intensity that matches the drive mode being executed is applied to the driver in the case where the determination unit 13 determines that it is necessary to call attention. Consequently, stimuli at different intensities can be applied to the driver in accordance with the drive mode. Hence, since the intensity of a stimulus is determined in consideration of the drive mode in contrast to a case where a stimulus at a constant intensity is applied to the driver without consideration of the drive mode, for example, it is possible to suppress the driver feeling annoyed with a stimulus applied to the driver to call attention.

Modifications

While an embodiment of the disclosure has been described above, the disclosure is not limited to the embodiment discussed above. The disclosure can be implemented in various forms in which a variety of modifications and alterations are made based on the knowledge of a person skilled in the art, besides the embodiment discussed above.

For example, while the retractor 4 is indicated as an example of the stimulus application device in the embodiment described above, the disclosure is not limited thereto.

The attention calling may be at least one of light irradiation, sound, and physical stimuli such as vibration applied to prompt the driver to check driving and the surroundings. Therefore, the stimulus application device may be an interior light directed toward the driver, an in-vehicle speaker, and a vibrator in a seat surface, etc., for example. The control unit may be a functional component of the attention calling ECU 10 that can control such a stimulus application device so as to apply a stimulus at an intensity that matches the drive mode being executed to the driver in the case where the determination unit determines that it is necessary to call attention.

The driver state recognition unit 12 recognizes, as examples of the driver state, the driver looking away, a reduced degree of attentiveness of the driver, and the driver driving carelessly. However, the driver state is not limited thereto. The driver state may be any state of the driver that can be utilized by the determination unit 13 to determine whether it is necessary to call attention.

In the embodiment described above, the intensity ST2 is higher than the intensity ST1, and the intensity ST3 is higher than the intensity ST2. However, the disclosure is not limited thereto. For example, the intensity ST2 may be equivalent to the intensity ST1 and the intensity ST3 may be higher than the intensity ST2, or the intensity ST2 may be higher than the intensity ST1 and the intensity ST3 may be equivalent to the intensity ST2.

What is claimed is:

1. An attention calling device configured to call attention of a driver of a vehicle with a drive mode switchable among manual driving, drive assist, and driver-centered automated driving, the attention calling device comprising:
    a drive mode recognition unit configured to recognize the drive mode being executed;
    a driver state recognition unit configured to recognize a driver state, which is a state of the driver, based on a captured image from a driver monitor camera provided in the vehicle;
    a determination unit configured to determine based on the driver state whether it is necessary to call the attention; and
    a control unit configured to control a stimulus application device of the vehicle so as to apply a stimulus at an intensity that is selected based on the drive mode being executed to the driver to direct an attention of the driver to driving of the vehicle in the case where the determination unit determines that it is necessary to call the attention.

2. A attention calling device comprising at least one processor, wherein
    the processor is configured to:
        recognize a drive mode being executed in a vehicle;
        recognize a driver state which is a state of a driver of the vehicle;
        determine based on the driver state whether it is necessary to call attention; and
        output a signal for applying a stimulus at an intensity that is selected based on the drive mode being executed to the driver to direct an attention of the driver to driving of the vehicle in the case where it is determined that it is necessary to call the attention.

3. The attention calling device according to claim 2, wherein
    the processor is configured to output the signal so as to make the intensity of the stimulus which is applied to the driver higher as the drive mode being executed is a drive mode that provides less opportunities for the driver to be involved in drive operations for the vehicle.

4. The attention calling device according to claim 3, wherein:
    the drive mode includes manual driving, drive assist, and driver-centered automated driving; and
    the processor is configured to:
        output the signal such that the intensity of the stimulus which is applied to the driver in the case where the drive mode is the manual driving is less than that of the stimulus which is applied in the case where the drive mode is the drive assist; and
        output the signal such that the intensity of the stimulus which is applied to the driver in the case where the drive mode is the drive assist is less than that of the stimulus which is applied in the case where the drive mode is the driver-centered automated driving.

5. The attention calling device according to claim 4, wherein:
    the drive mode includes system-centered automated driving; and
    the processor is configured to output the signal such that the intensity of the stimulus which is applied to the driver in the case where the drive mode is the system-centered automated driving is less than that of the stimulus which is applied in the case where the drive mode is the driver-centered automated driving.

6. A attention calling system comprising:
    a camera configured to acquire a captured image of a driver of a vehicle;
    a stimulus application device configured to apply a stimulus to the driver; and
    at least one processor, wherein:
    the processor is configured to:
        recognize a drive mode being executed in the vehicle;
        recognize a driver state, which is a state of the driver, based on the image which is acquired by the camera;
        determine based on the driver state whether it is necessary to call attention; and
        control the stimulus application device so as to apply a stimulus at an intensity that is selected based on the drive mode being executed to the driver to direct an attention of the driver to driving of the vehicle in the case where it is determined that it is necessary to call the attention.

7. The attention calling system according to claim 6, wherein
    the processor is configured to make the intensity of the stimulus which is applied to the driver higher as the drive mode being executed is a drive mode that provides less opportunities for the driver to be involved in drive operations for the vehicle.

8. The attention calling system according to claim 7, wherein:
    the drive mode includes manual driving, drive assist, and driver-centered automated driving; and
    the processor is configured to:
        control the stimulus application device such that the intensity of the stimulus which is applied to the driver in the case where the drive mode is the manual driving is less than that of the stimulus which is applied in the case where the drive mode is the drive assist; and
        control the stimulus application device such that the intensity of the stimulus which is applied to the driver in the case where the drive mode is the drive assist is less than that of the stimulus which is applied in the case where the drive mode is the driver-centered automated driving.

9. The attention calling system according to claim 8, wherein:
   the drive mode includes system-centered automated driving; and
   the processor is configured to control the stimulus application device such that the intensity of the stimulus which is applied to the driver in the case where the drive mode is the system-centered automated driving is less than that of the stimulus which is applied in the case where the drive mode is the driver-centered automated driving.

10. The attention calling system according to claim 6, wherein:
   the stimulus application device is a retractor configured to wind a seatbelt; and
   the retractor is configured to wind the seatbelt more strongly as the intensity of the stimulus which is applied to the driver is higher.

* * * * *